United States Patent [19]
Bricault, Jr. et al.

[11] Patent Number: 5,520,664
[45] Date of Patent: May 28, 1996

[54] CATHETER HAVING A LONG-LASTING ANTIMICROBIAL SURFACE TREATMENT

[75] Inventors: Raymond J. Bricault, Jr., West Boylston; John E. Barry, Malden; Piran Sioshansi, Lincoln, all of Mass.

[73] Assignee: Spire Corporation, Bedford, Mass.

[21] Appl. No.: 180,148

[22] Filed: Jan. 11, 1994

Related U.S. Application Data

[63] Continuation-in-part of Ser. No. 780,275, Oct. 18, 1991, abandoned, Ser. No. 894,822, Jun. 8, 1992, abandoned, and Ser. No. 6,749, Jan. 21, 1993, abandoned, which is a division of Ser. No. 663,361, Mar. 1, 1991, abandoned.

[51] Int. Cl.$^6$ .................................................. A61M 5/32
[52] U.S. Cl. ........................... 604/265; 604/174; 604/280
[58] Field of Search ...................... 604/265, 280, 604/174; 623/1, 11, 901; 428/457, 35.7

[56] References Cited

U.S. PATENT DOCUMENTS

| | | | |
|---|---|---|---|
| 3,557,795 | 1/1971 | Hirsch | 128/335.5 |
| 3,589,975 | 6/1971 | Andrews et al. | 161/165 |

(List continued on next page.)

FOREIGN PATENT DOCUMENTS

| | | |
|---|---|---|
| 0029787 | 11/1980 | European Pat. Off. |
| 86107598 | 12/1986 | European Pat. Off. |
| 206024A | 12/1986 | European Pat. Off. |
| 87307136 | 3/1988 | European Pat. Off. |
| 3228849A | 8/1982 | Germany . |
| 3302567A | 1/1983 | Germany . |
| 3228849 | 2/1984 | Germany . |
| 3830359 | 12/1989 | Germany . |
| 4328999 | 3/1995 | Germany . |
| PCT/CA91/ 00453 | 7/1992 | WIPO . |
| PCT/US92/ 08266 | 4/1993 | WIPO . |
| PCT/US93/ 00685 | 8/1993 | WIPO . |
| PCT/WO93/ 23092 | 11/1993 | WIPO . |
| PCT/CA93/ 00201 | 11/1993 | WIPO . |

OTHER PUBLICATIONS

Maki et al.(Dec. 1973) "Infection Control in Intravenous Therapy," *Ann. Int. Med.*, 79:867–887.

Tully et al. (Mar. 1981) "Complications of Intravenous Therapy with Steel Needles and Teflon® Catheters", *Am. J. Med.*, 70:702–706.

Friedland (1984) "Infusion–Related Phlebitis —Is the In–Line Filter the Solution?", *N.E. J. Med.*, 312:113–115.

Falchuk et al. (1984) "Microparticulate–Induced Phlebitis", *N.E. J. Med.*, 312:78–82.

Lewis et al. (1985) "Assessment of thromboresistance of intravenous cannulae by $^{125}$I– fibrinogen scanning", *J. Biomed. Mat. Res.*, 19:99–113.

Power et al. (Jul. 1986) "Fatal Bacterial Endocarditis as a Complication of Permanent Indwelling Catheters", *Am. J. Med.*; 81:166–168.

Elliott (May 1988) "Intravascular–device infections", *J. Med. Microbiol.*, 27:161–167.

Bentivegna (Aug. 1989) "The Vitacuff and Intravascular Catheter–Related Infection", *JAMA Letters*, 262:613–614.

(List continued on next page.)

*Primary Examiner*—C. Fred Rosenbaum
*Assistant Examiner*—Mark Bockelman
*Attorney, Agent, or Firm*—Thomas J. Engellenner; John V. Bianco; Lahive & Cockfield

[57] ABSTRACT

Catheters including at least one component having a tissue interfacing surface characterized by a substantially non-leaching surface treatment of antimicrobial metal. The component can be a subcutaneous cuff, and the antimicrobial metal can be silver. The process for implanting the silver atoms can include dry coating the tissue interfacing surface of the catheter by way of ion beam assisted deposition. Alternatively, the silver can be introduced into the tissue interfacing surface by ion implantation.

35 Claims, 7 Drawing Sheets

U.S. PATENT DOCUMENTS

| | | | |
|---|---|---|---|
| 3,695,921 | 10/1972 | Shepherd et al. | 117/72 |
| 3,699,956 | 10/1972 | Kitrilakis et al. | 128/348 |
| 4,027,393 | 1/1977 | Ellis . | |
| 4,039,699 | 8/1977 | Morimoto et al. | 427/38 |
| 4,054,139 | 10/1977 | Crossley | 128/260 |
| 4,152,478 | 5/1979 | Takagi | 428/221 |
| 4,253,463 | 3/1981 | Kim | 128/348 |
| 4,281,029 | 7/1981 | Takagi et al. | 427/38 |
| 4,374,717 | 2/1983 | Drauglis et al. | 204/192 C |
| 4,388,164 | 6/1983 | Kolev et al. | 204/192 SP |
| 4,411,648 | 10/1983 | Davis et al. | 604/21 |
| 4,440,108 | 4/1984 | Little et al. | 118/719 |
| 4,443,488 | 4/1984 | Little et al. | 427/38 |
| 4,452,827 | 6/1984 | Kolev et al. | 427/38 |
| 4,476,590 | 10/1984 | Scales et al. | 3/1.91 |
| 4,479,795 | 10/1984 | Mustacich et al. | 604/53 |
| 4,581,028 | 4/1986 | Fox, Jr. et al. | 623/2 |
| 4,592,920 | 6/1986 | Murtfeldt | 427/2 |
| 4,683,149 | 7/1987 | Suzuki et al. | 427/38 |
| 4,693,760 | 9/1987 | Sioshansi | 148/4 |
| 4,718,905 | 1/1988 | Freeman | 623/6 |
| 4,743,308 | 5/1988 | Sioshansi et al. | 148/4 |
| 4,743,493 | 5/1988 | Sioshansi et al. | 428/217 |
| 4,846,834 | 7/1989 | von Recum et al. | 623/11 |
| 4,855,026 | 8/1989 | Sioshansi | 204/192.11 |
| 4,871,366 | 10/1989 | von Recum et al. | 623/11 |
| 4,872,922 | 10/1989 | Bunker et al. | 148/4 |
| 4,886,505 | 12/1989 | Haynes et al. | 604/265 |
| 4,923,450 | 5/1990 | Maeda et al. | 604/265 |
| 4,936,281 | 6/1990 | Stasz | 128/660.03 |
| 4,994,060 | 2/1991 | Rink et al. | 606/28 |
| 5,049,140 | 9/1991 | Brenner et al. | 604/266 |
| 5,057,106 | 10/1991 | Kasevich et al. | 606/33 |
| 5,067,491 | 11/1991 | Taylor, II et al. | 128/748 |
| 5,069,227 | 12/1991 | Maronian | 165/173 |
| 5,152,273 | 10/1992 | Suzuki et al. | 623/1 |
| 5,165,952 | 11/1992 | Solomon et al. | 427/2 |
| 5,223,309 | 6/1993 | Farivar | 427/525 |
| 5,236,509 | 8/1993 | Sioshansi et al. | 118/719 |
| 5,308,704 | 5/1994 | Suzuki et al. | 427/525 |

OTHER PUBLICATIONS

Liedberg et al. (Jan. 1989) "Assessment of Silver–Coated Urinary Catheter Toxicity by Cell Culture" *Urol. Reg.*, 17:359–360.

Solnick–Legg et al. (Apr. 1989) "Ion Beam and Plasma Technology for Improved Biocompatible Surfaces", MRS Bulletin, pp. 27–30.

Corona et al. (Jul. 1990) "Infections Related to Central Venous Catheters", *Mayo Clin. Proc.*, 65:979–986.

Johnson et al. (Nov. 1990) "Prevention of Catheter–Associated Urinary Tract Infection with a Silver Oxide–Coated Urinary Catheter: Clinical and Microbiologic Correlates", *J. Infect. Dis.*, 162:1145–1150.

Liedberg et al. (1990) "Silver Alloy Coated Catheters Reduce Catheter–Associated Bacteriuria", *Brit. J. Urol.*, 65:379–381.

Putterman (1990) "Central venous catheter related sepsis: A clinical review", *Resusciation*, 20:1–16.

Haywood "Dual IBAD Makes Good Coatings", *Advanced Materials and Processes*, vol. 138, Issue 6, publication of The Materials Information Society, (Feb. 6, 1991).

Mahan et al. (Mar. 1991) "Factors in Pin Tract Infections", *Orthopedics*, 14:305–308.

Murphy et al. (Mar. 1991) "The Small Pin Circular Fixator For Proximal Tibial Fractures With Soft Tissue Compromise", *Orthopedics*, 14:273–280.

IBAD Brochure, Spire Corporation, Bedford, MA, published Mar. 8, 1991.

SPI–ARGENT™ Technical Brochure, published Apr. 23, 1993.

SPI–ARGENT™ Brochure, published Oct. 9, 1992.

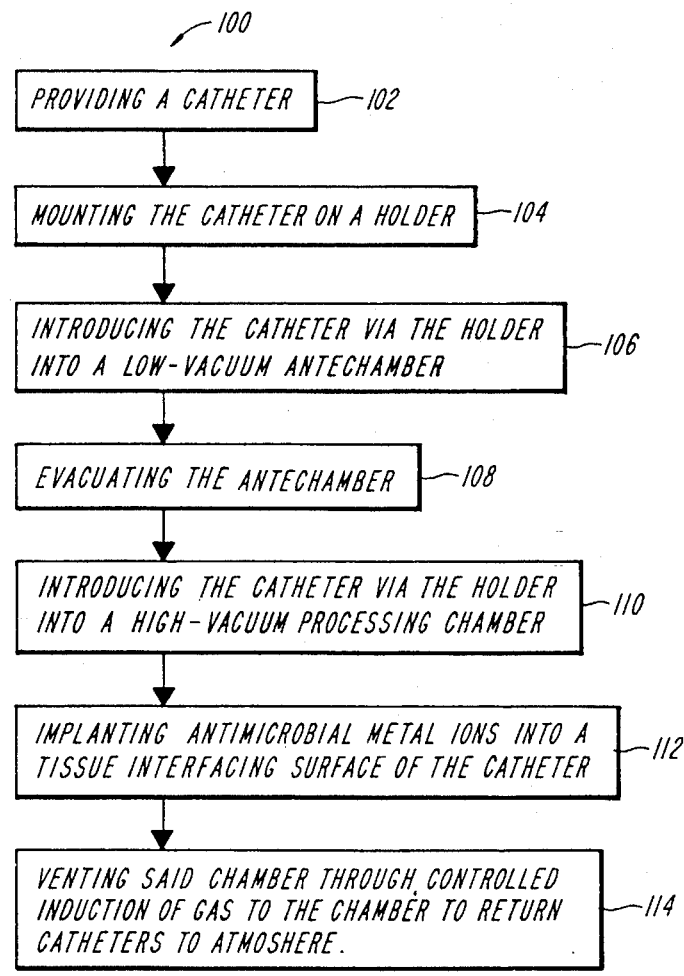
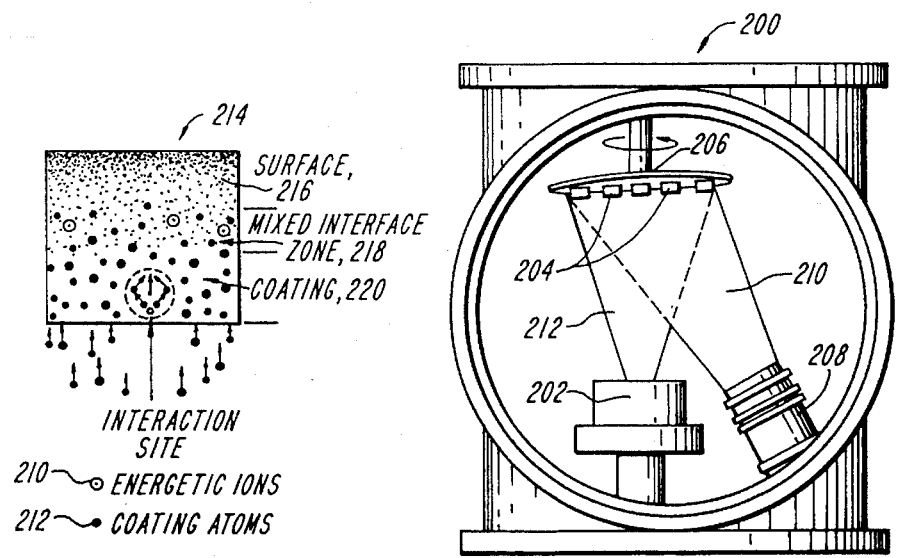
FIG. 1
FIG. 2A
FIG. 2B

5,520,664

CATHETER HAVING A LONG-LASTING ANTIMICROBIAL SURFACE TREATMENT

REFERENCE TO RELATED PATENTS

This application is a continuation-in-part of U.S. patent application Ser. No. 08/006,749, filed Jan. 21, 1993, entitled "Metallized Polymeric Implants, Method And Apparatus," now abandoned which is itself a divisional of U.S. patent application Ser. No. 07/663,361, filed Mar. 1, 1991, entitled "Metallized Polymeric Implants, Method And Apparatus," now abandoned. This application is also a continuation-in-part of U.S. patent application Ser. No. 07/780,275, filed Oct. 18, 1991, entitled "Bactericidal Coatings For Implants," now abandoned and U.S. patent application Ser. No. 07/894,822, filed Jun. 8, 1992, entitled "Infection Resistant Medical Devices And Process" now abandoned. The above cited patent applications, assigned to a common assignee, Spire Corporation, Bedford, Mass., are incorporated herein by reference.

BACKGROUND OF THE INVENTION

The present invention relates generally to polymeric implants. More particularly, the invention relates to an improved catheter incorporating antimicrobial metal atoms to create a bactericidal/fungicidal surface treatment on a tissue contacting surface.

Central venous catheters are indispensable tools in modem medicine. It has been estimated that over one-fourth of patients hospitalized in the U.S.A. receive treatments via central venous catheters. For example, catheters are used for quick delivery of nutrient fluids, chemotherapy, and accurate measurement of central venous pressure.

Despite their utility, a variety of complications are associated with catheter use. Such complications include air embolisms, catheter-related sepsis (CRS), clot formation at the catheter tip, cardiac arrhythmia, and injury to peripheral nerves or blood cells. Additionally, the use of polymeric catheters has brought with it an increase in reports of complications, such as thrombophlebitis and sepsis.

It has been estimated that catheter-related sepsis or CRS occurs at a rate of 6 to 8 per 1000 catheter days, with a mortality rate of 10 to 20%. The classically accepted cause of CRS is bacterial migration and colonization along the catheter from the skin entry site. Not surprisingly, most bacteria found to cause CRS, such as the Staphylococcus species, commonly populate the skin.

Replacing the catheter at frequent intervals during treatment is a potential solution to CRS. Unfortunately, since there is no way to make a diagnosis before removing the catheter, this often results in removal of sterile catheters. Furthermore, since additional catheterization is potentially traumatic, doctors prefer to avoid it. Replacing the catheter with a new one over a guidewire eliminates the necessity of additional catheterization, but there is not presently enough data to verify that this technique reduces infection.

Since CRS is believed to be caused by migration of bacteria from the skin, it was thought that the use of wound dressings and topical antibiotics would reduce CRS. One approach has been to use Opsite™ type dressings, comprising a clear adhesive-backed membrane which has been shown to discourage bacterial growth. While the Opsite™ type dressing has proved somewhat effective in reducing insertion site colonization and infection, its use has been associated with wound and system infection outbreaks, and it is still considered experimental. Topical antibiotics have also been used at the catheter insertion site, but results of these studies have been conflicting. In a few cases, there were actually increases of some bacterial and fungal strains with the use of certain antibiotics.

In another approach, some catheter manufacturers have resorted to coating the entire length of the catheter with an antimicrobial metal or metal salt. Such catheters, known for example, as Bioguard® or Arrowguard® coated catheters, function to prevent infections by leaching silver or similar metals into the tissue and interstitial spaces around the catheter, thereby creating a toxicity zone which inhibits microbial migration. One common silver salt used for such controlled release applications is silver sulphadiazine. When this salt is exposed to physiological conditions, silver or silver ions are released into the zone surrounding the device.

Yet another promising technique for reducing CRS is the application of a subcutaneous cuff. Typically, the cuff is made from a porous material such as polyester and is placed around the catheter in the subcutaneous tissue such that tissue can grow into it. The ingrown tissue anchors the catheter in place and serves as a barrier to bacterial migration from the skin. By inhibiting transdermal movement and providing a mechanical barrier, such cuffs discourage microbial migration. Polyester cuffs have been used as bacterial barriers for many years on devices such as Hickman® and Broviac® catheters. These cuffed catheters have been very successful in reducing infection, with incidence of infection reportedly down to one case per patient-year.

In addition to the Hickman® and Broviac® catheters, another cuff, the VitaCuff®, available from Vitaphore Corporation, has been developed to further improve catheter performance. This cuff is made of silicone elastomer which incorporates a collagen sponge with a silver compound distributed throughout its matrix. The silver is meant to act as an antimicrobial agent to further reduce the incidence of infection associated with catheter use. The infection resistance provided by the silver is related both to its ability to leach and to its ability to interfere with cell metabolism. Since the VitaCuff® leaches silver or silver ions into a volume of tissue surrounding the cuff, the coming is effective only for a limited period of time, on the order of 4–6 weeks, or until the collagen sponge and the subordinate silver is substantially exhausted.

Accordingly, an object of the present invention is to provide an improved catheter having antimicrobial properties.

An additional object of the present invention is to provide an improved catheter having antimicrobial properties which do not substantially degenerate over time.

A further object of the present invention is provide a device which exhibits antimicrobial properties for a longer period of time and performs in a manner that does not vary substantially over time for long time periods, e.g., on the order of months, or longer.

Another object of the invention is to provide an improved catheter which incorporates a subcutaneous cuff having specific antimicrobial properties.

Other general and specific objects of the invention will in part be obvious and will in part appear hereinafter.

SUMMARY OF THE INVENTION

The foregoing objects are attained by the invention, which provides a catheter including at least one component having a tissue contacting surface characterized by a substantially nonleaching surface treatment of an antimicrobial metal. As used herein, the term "antimicrobial" refers to any agent which acts to inhibit the growth of microorganisms, such as pathogenic bacteria, protists and/or fungi, which can cause infections within a patient if permitted to enter the patient's body through the catheter's skin entry site. According to one embodiment of the invention, the catheter includes a subcutaneous cuff which is treated with the antimicrobial metal. According to one aspect of the invention, the metal atoms are introduced into the catheter to a sufficient depth or otherwise sufficiently bound onto the catheter surface to ensure that the antimicrobial metal is substantially nonleaching. By creating a catheter having at least one tissue contacting surface on which an antimicrobial metal is bound in a long-lasting fashion, the present invention presents a more competent barrier to infection-causing microorganisms which is not predestined to decomposition or degradation as a result of the ionization and/or leaching of the antimicrobial metal into a volume of tissue in the manner of prior art devices.

In one preferred embodiment, the tissue contacting surface is also treated with at least one additional species of adhesion-promoting atoms which enhance the binding of the antimicrobial metal to the surface. The surface can also be treated with a species of barrier atoms which form a barrier to oxidation and/or retard galvanic reactions which might otherwise degrade the catheter's antimicrobial surface properties or reduce its functional lifetime. (As used herein the term "atom" is used to encompass not only neutral valence elements but also charged species of such elements.)

The present invention further encompasses methods of manufacturing long-lasting antimicrobial devices such as catheters and the like which incorporate antimicrobial metals onto or into their surfaces. By way of example, the antimicrobial metals can be implanted through a dry coating process which includes, introducing the catheter and/or the cuff component into a vacuum chamber system provided with both an ion source and an evaporator, and forming a metallic surface treatment on a tissue interfacing surface of the catheter. The surface treatment can be incorporated into the material by an ion beam process, such as an ion beam assisted deposition process (IBAD). Where an IBAD process is employed, an ion source accelerates ions into a growing film formed by physical vapor deposition. The resulting collisions mix the film atoms with the catheter surface and cause the film atoms to become embedded within and/or upon the tissue interfacing surface. An apparatus for dry coating the catheter with antimicrobial metal atoms can for example, comprise a vacuum chamber, at least a first ion source and an evaporator, all operatively mounted within the chamber. For an additional discussion of IBAD deposition techniques, one should refer to U.S. Pat. No. 5,236,509, entitled "Modular IBAD Apparatus For Continuous Coating," the contents of which are incorporated herein by reference. For a discussion of other related approaches, one should refer to U.S. Pat. No. 4,855,026, entitled "Sputter Enhanced Ion Implantation Process," the contents of which are also incorporated herein by reference.

The dry coating apparatus can further include a second ion source. Preferably, the first ion source is a relatively low energy ion source in comparison to the second ion source. During operation, the low energy ion source can clean and/or texture the surface to be coated. Subsequently, the high energy ion source and an evaporated species can be directed at the surface to affect implantation. Alternatively, either source can individually clean the surface with appropriate adjustments to the processing conditions.

By way of further example, the antimicrobial metal can also be implanted using a suitable high current ion implanter, such as a Varian-Extrion 200 kV implanter, an Eaton-Nova implanter, or like instrument. Where such an ion implantation apparatus is employed, antimicrobial metal ions are accelerated toward the tissue interfacing surface. As the metal ions collide with the catheter surface, they become embedded below the surface. Additionally, a thin, modified, surface layer is formed. For a more detailed discussion of such an ion implanter, one should refer to U.S. Pat. No. 4,693,760, entitled "Ion Implantation Of Titanium Workpieces Without Discoloration," the contents of which are incorporated herein by reference.

BRIEF DESCRIPTION OF THE DRAWINGS

For a fuller understanding of the nature and objects of the present invention, reference should be made to the following detailed description and the accompanying drawings, in which:

FIG. 1 is a flow diagram of a dry coating process for implanting antimicrobial metal atoms into a tissue interfacing surface of a catheter;

FIGS. 2a and 2b depict an ion beam assisted deposition apparatus for practicing the process of FIG. 1;

DETAILED DESCRIPTION

Figure 3:
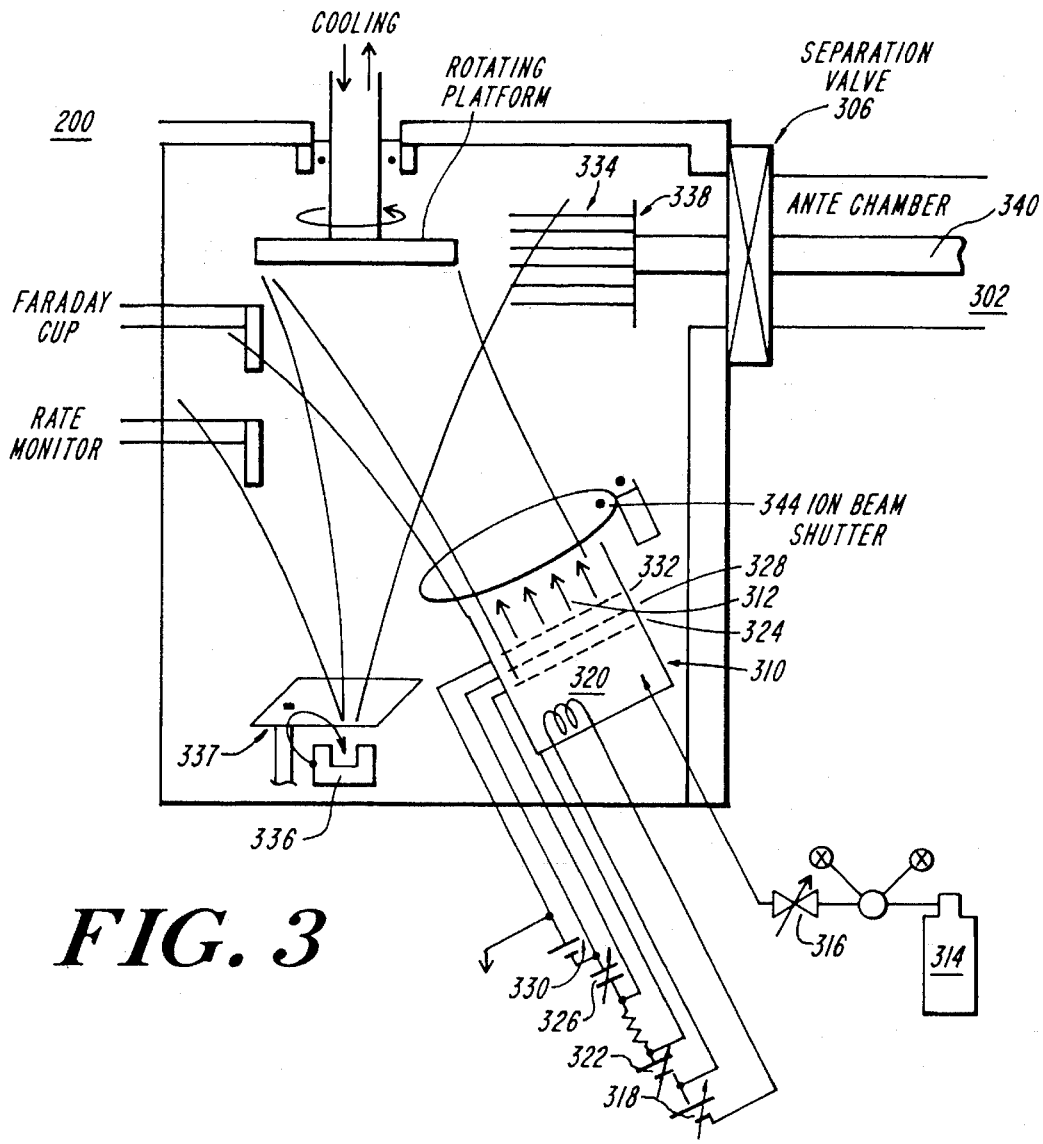
FIG. 3. is a schematic diagram of the ion beam assisted deposition apparatus of FIG. 2.

The present invention relates generally to polymeric implants, such as cannulae, catheters, percutaneous connectors and the like. More particularly, the invention relates to an improved catheter treated with a substantially nonleaching antimicrobial metal to enhance the bactericidal/fungicidal properties of a tissue interfacing surface. As used herein, the term "antimicrobial metal" refers to atoms or molecules which exhibit antimicrobial properties, wherein such metals include chromium, zirconium, aluminum, nickel, tungsten, molybdenum, tantalum, platinum, palladium, iridium, gold, silver, mercury, copper, zinc, cadmium, and alloys and compounds thereof.

FIG. 1 shows a flow diagram 100 of a dry coating process for implanting antimicrobial metal atoms to form a bactericidal/fungicidal component on a tissue interfacing surface of a catheter or catheter portion. This process essentially comprises the steps of providing 102 a catheter to be implanted with the metal atoms, mounting 104 the catheter on a holder, optionally introducing 106 the catheter via the holder into a low-vacuum antechamber, evacuating 108 the low-vacuum antechamber to a high vacuum, further introducing 110 the catheter via the substrate into a high-vacuum processing chamber, and implanting 112 antimicrobial metal atoms into a tissue interfacing surface of the catheter by a dry coating method within the high-vacuum processing chamber. In some instances, the use of a low vacuum antechamber can be eliminated if economic performance is not an issue or the main chamber is designed to accommodate large pressure changes. Upon completion, the device is removed 114. Preferably, the dry coating method is an ion-beam process, such as an ion beam assisted deposition (IBAD) process.

FIG. 2 shows a system 200 for performing ion beam assisted deposition (IBAD) according to the process of FIG. 1. The system 200 combines physical vapor deposition with ion beam bombardment in a high vacuum environment (e.g., a base vacuum on the order of about $10^{-5}$ torr or less). The electron beam evaporator 202 generates a vapor flux of atoms 212. Those atoms are deposited on catheters 204, which are held in place by the rotatable holder 206. Simultaneously with the evaporator 202 generating the flux of atoms 212, the ion source 208 accelerates ions 210 into the growing film at energies of several hundred to several thousand electron volts. As can be seen from the magnified view 214 of the surface 216, the energetic ions 210 collide with the coating atoms 212. Such collisions cause the coating atoms 212 to become embedded onto and below the surface 216 thus, forming a substantially nonleaching surface treatment. The surface treatment includes the coating 220, the mixed interface zone 218, and the tissue interfacing surface itself 216.

An object of the present invention is to lengthen the time period over which the component implanted with the antimicrobial metal exhibits antimicrobial properties. Thus, according to one preferred embodiment, the metallic surface treatment is substantially nonleaching. As defined herein, substantially nonleaching refers to the property that, while the catheter exhibits antimicrobial properties when put in contact with microorganisms such as *E. coli, P. aeruginosa,* and *S. epidermidis,* the growth of these organisms is virtually unaffected at a distance greater than 4 mm from the film. Thus, a component that includes a substantially nonleaching metal surface treatment according to the invention generates a release of that metal into saline and/or Ringer's solution of not more than one microgram per day per square centimeter surface area. As a result, the component's antimicrobial properties last a minimum of two months and many last for years. To achieve a substantially nonleaching surface treatment, in the illustrative example of FIG. 2, the atoms 212 are embedded in the material of the catheter and the atomic penetration extends below the surface 216. In one preferred embodiment, the antimicrobial metal is introduced into the surface as ions or in elemental form. Such surface treatments can extend approximately 0.01 micrometer to approximately 5 micrometers.

When the catheter or catheter component is a solid polymer and an IBAD deposition technique is employed, it is preferable for the atoms to extend about 0.01 micrometers to about 0.5 micrometers into the polymeric material. This penetration will be accompanied by a surface build-up of the antimicrobial atoms as well. If an ion implanter is used, as described in more detail below, the antimicrobial metal will penetrate further, for example from about 0.01 micrometers to about 5.0 micrometers with somewhat less surface build-up. When the catheter component to be treated is porous, such as for example, a polyester felt or fibrous cuff component or another material having interstitial spaces, the antimicrobial metal will penetrate into the fibers (or other solid components of the material) to depths comparable to those of solid polymers, but also will be accompanied by deeper penetration of some atoms due to the porous nature (and interstitial spaces) of the material. Regardless of the actual penetration depth, the present invention provides techniques which ensure that the deposited or implanted antimicrobial metal is firmly anchored in place so as to provide a long-lasting, surface-directed antimicrobial effect, rather than a temporary volumetric effect that is lost after a short period of time due to leaching of the active antimicrobial agent from the device.

As it can be seen, the system 200 overcomes many of the limitations of conventional physical vapor deposition processes and produces exceptionally high quality surface treatments that are ultra-adherent. Additionally, the above described ion beam assisted deposition is achieved at relatively low temperatures (often below 100° C.), and can therefore be used to treat thermally sensitive materials such as the medical grade polymers used to make catheters. These techniques also allow one to modify the physical structure of the metallic treatment on the catheter or catheter component surface to be finely dispersed, amorphous and/or microcrystalline.

FIG. 3 shows a schematic diagram of the system 200 of FIG. 2. The apparatus 200 is designed for implanting devices, such as cannula, needles, catheters and associated subcutaneous cuffs, percutaneous connectors, fluid delivery and removal tubes, and the like. As shown in FIG. 3, the apparatus 200 essentially comprises a vacuum chamber system formed from low-vacuum antechamber 302 and a high vacuum processing chamber 304, air-tightly separated from each other by a gate 306 movable between a shown open position and a closed position shown by dashed lines 308.

An ion source 310, preferably a bucket type ion source, is mounted within the high-vacuum processing chamber 304 in a position below antechamber 302, substantially as shown. As shown, the source 310 of ions 312 is fed by one or more gases, such as argon, neon and/or helium, from a suitable gas supply source 314, via a mass flow controller 316, regulating the rate of gas feed. A filament power supply 318 is provided to supply current to the filaments 320. The apparatus 200 also includes an arc supply 322 to maintain an arc discharge between the anode 324 and the filaments 320, an exit power supply 326 to accelerate the ions through the accelerator grid 328 of the multiple grid system of the bucket type ion source 310, and a suppressor power supply 330 for negatively biasing the suppresser grid 332 of the ion source 310 to reduce backstreaming of secondary electrons from the catheters 334.

An evaporator 336 also is mounted in the high-vacuum processing chamber 304 in operative association with the ion source 310. The evaporator 336 is designed to vaporize particular metallic evaporants so as to dry-coat the catheter 334 therewith, being assisted in the dry-coating by the ion beam 312 emanating from the ion source 310. The evaporants can include chromium, cadmium, zirconium, aluminum, nickel, tungsten, molybdenum, tantalum, titanium, platinum, palladium, carbon, iridium, gold silver, mercury, copper, zinc and alloys, and compounds thereof. Additionally, according to the invention, more than one of the above metals can be implanted into the catheter 334. A vapor shutter 337, designed to be rotated in and out of place of the evaporator 336, shields the substrate from the evaporants when in place. Catheters 334 to be dry-coated are introduced into the vacuum chambers 302 and 304 with the aid of a suitable catheter holder 338.

Preferably, the catheter holder 338 is mounted for both rotational and translatory motion on a shaft 340 and is introduced into the antechamber 302 through translation and/or extraction from the antechamber 302 via shaft 340. A pivotable shutter 344 is provided to shield the catheters 334 from the ion beam 312, when desired. A thickness monitor 346 preferably is provided in operative association with the holder 338 to monitor the thickness of the thin metallic film being deposited on the catheters 334 during operation of the dry-coating apparatus 200

Figure 4:
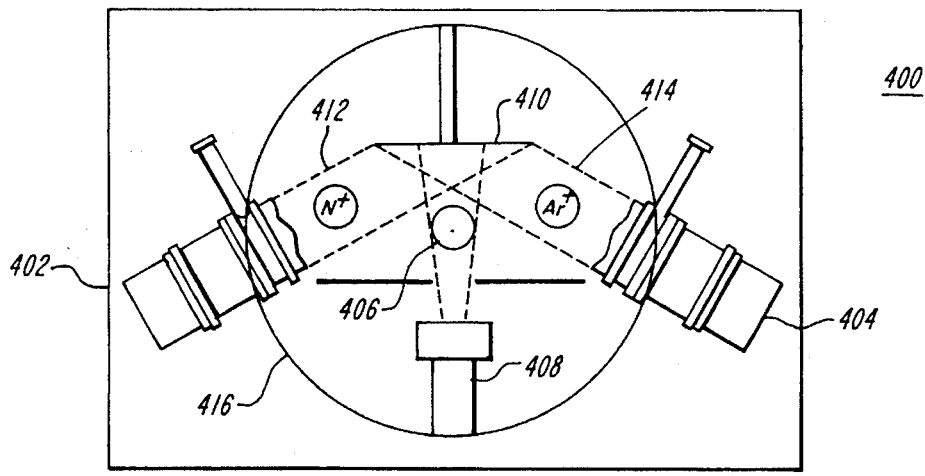
FIG. 4 depicts an alternative ion beam assisted deposition apparatus for practicing the process of FIG. 1.

FIG. 4 shows an alternative embodiment 400 of the IBAD apparatus of FIG. 2. As in the case of the apparatus 200, the apparatus 400 combines physical vapor deposition with ion beam bombardment. However, the system 400 includes two ion beam sources; a high energy ion source 402 and low energy ion source 404. In the dual IBAD apparatus 400, the evaporated species 406, generated by evaporator 408, converges on the substrate 410 along with ion beams 412 and 414.

According to one embodiment of the invention, dual IBAD is employed to form a substantially nonleaching surface treatment of an antimicrobial agent such as silver, on for example, a catheter formed from polymeric materials. Traditionally, polymers bond poorly to metals, and whatever interfacial bonding occurs rarely can withstand water diffusion for an extended time. However, with IBAD, the ion irradiation disrupts the structure of chemical/physical bonding of interface atoms. Consequently, such a process creates an adhesion layer where metal and polymer atoms attain stability. In addition, energetic ions "bombard" the evaporated atoms, which in turn, are driven into the polymer by elastic recoil to develop an adhesive transition zone. One significant advantage of employing dual ion beams 412 and 414, is that they enhance the formation of a superior adhesive transition zone.

According to one preferred embodiment, the system 400 comprises a cryo pumped high-vacuum chamber 416 facilitating a four crucible electron-beam evaporator 408 with an average deposition rate of approximately one to fifty angstroms/sec. The two ion sources 402 and 404 are offset 30° on either side of the evaporator 408. The high-energy ion source 402 has an acceleration voltage of 5 to 40 kV and a current density of up to 40 mA on a 150 mm² substrate. The low-energy ion source 404 has a current density of 100 mA at a maximum acceleration voltage of 2 kV. As those skilled in the art will appreciate, although not shown, the system 400 also includes programmable controllers, power supplies, vacuum pumps, a closed loop water recirculator and a gas control system.

During operation, a surface to be treated is precleaned in either an ultrasonic solvent or another medium, depending upon material type. Next, the surface is affixed in the chamber 416 in such a way that facilitates proper cooling, rotation, and surface purity. The low energy ion beam 414 which can be, by way of example Ar+, is initially used to ion-sputter clean the substrate or to impart a specific unique texture to which the coating will be applied. Next, the high-energy 412 ion beam which can be, by way of example Ar+ or N+, and an evaporated species such as Cr+ are directed at the substrate. As a result, a primary intermixing of deposited molecules $Cr_xN_y$ occurs. The high-energy ion beam 412 can be controlled at least in part by varying the environmental compositions, using for example a residual gas analyzer, until the precise film stoichiometry is achieve, for example CrN.

Figure 5:
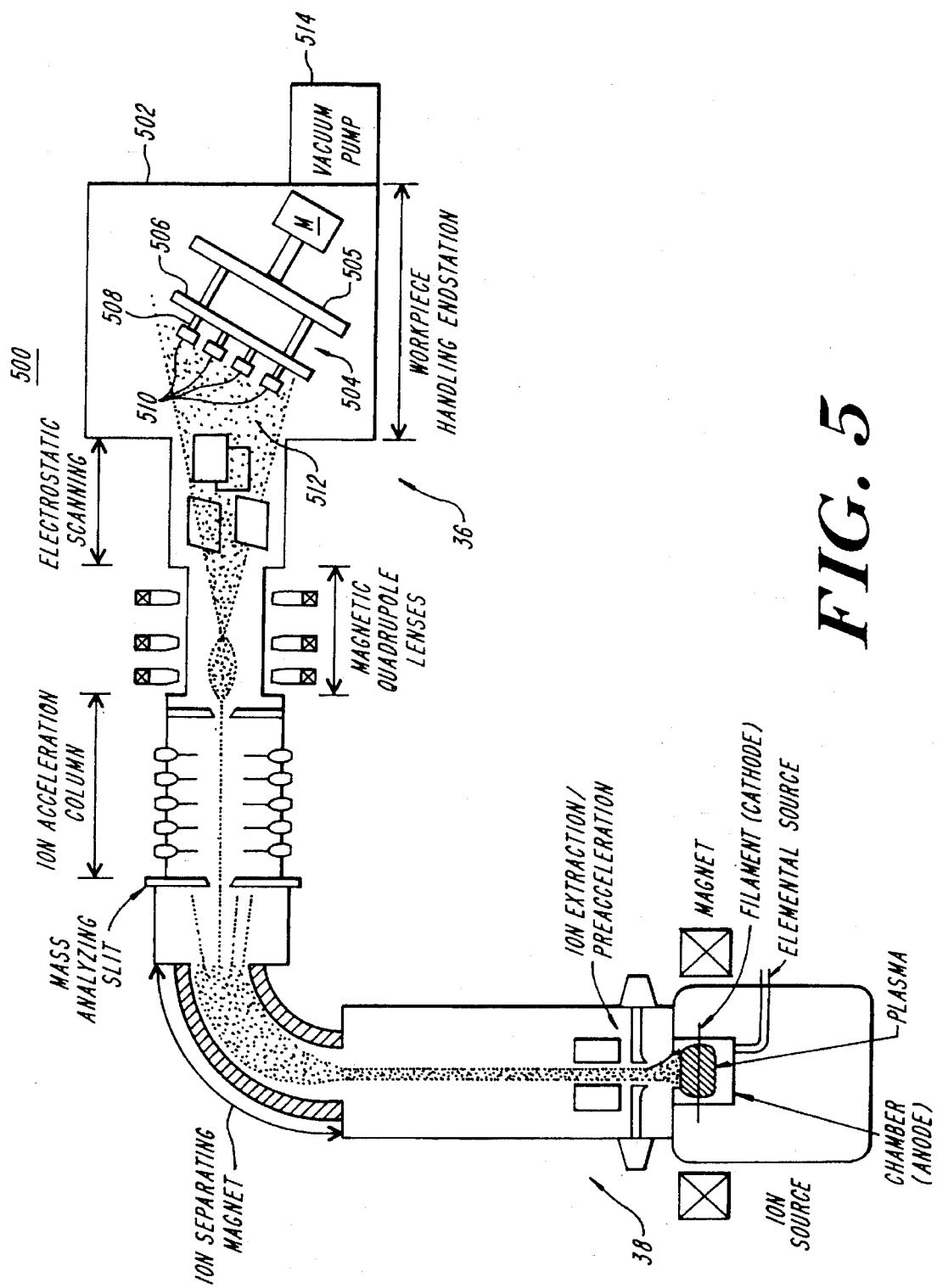
FIG. 5 is a schematic diagram of an alternative ion implantation apparatus for introducing antimicrobial metal atoms into a tissue interfacing surface of a catheter.

FIG. 5 shows a schematic diagram of an ion implanter 500 for introducing an antimicrobial metal into a tissue interfacing surface of a catheter. The ion implanter 500 can be the same as, or an adaptation of the one illustrated in and described in U.S. Pat. No. 4,693,760, previously incorporated by reference.

Within the processing chamber 502, a suitable fixture 504 is mounted on a base 505 designed for rotation by a suitable motor (M) and for cooling a base plate 505. On the base plate 505 preferably are mounted a plurality of appropriately shaped workpiece holders 508, each preferably consisting of plates designed to hold a multiplicity of parts. These workpiece holders 508 are designed to hold securely a plurality of catheters 510 and directly to expose these catheters 510 to an incoming ion beam 512 of antimicrobial metal ions. The shape of the particular workpiece holders 512 secured to the base plate 505 will of course depend upon the shape of the catheters 510.

With the catheters 510 properly secured within the chamber 502, a required vacuum environment within the processing chamber 502 is created by means of a vacuum pump 514, operatively connected to the chamber 502. With the aid of the pump 514, the processing chamber 502 is preferably evacuated to a vacuum pressure of at least $10^{-5}$ torr. Preferably, the vacuum pump 514 is an oil-free type designed to avoid the possibility of introducing surface contamination onto the catheters 510 to be ion implanted.

The surface of the catheters 510 is then exposed to the beam 512 of antimicrobial metal ions so as to create the subsurface graded fungicidal/bactericidal stratum therein. Preferably, the ion beam 512 possesses an energy from about 5 keV to about 200 keV, delivering a dose from about $5 \times 10^{13}$ to about $5 \times 10^{17}$ ions per square centimeter. The above mentioned ion beam energy and ion dose are intended to achieve a current density on the respective surface of the catheter 510 from about 0.01 microampere per square centimeter to about 20 microamperes per square centimeter.

Figure 6A:
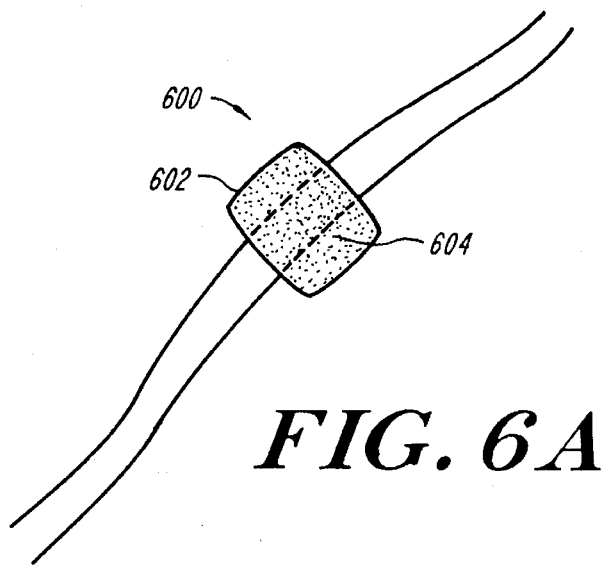
FIG. 6A shows a segment of a catheter including a subcutaneous cuff portion treated with an antimicrobial metal.

FIG. 6A shows a segment 600 of a catheter, including a subcutaneous cuff portion 602. The cuff 602 can be made from any relevant biocompatible materials. By way of example, but not limitation, such materials can include polyester, silicone, polyurethane, and fluoropolymer-based materials. As used herein, the term "biocompatible material" is used generally to encompass materials which do not induce substantial inflammatory or allergic reactions, systemic shock or toxicity. The cuff 602 is preferably formed from a porous material configuration, such as felt or velour. As is well known, porous materials allow subcutaneous tissue to grow into the cuff 602. The ingrown tissue anchors the catheter 600 in place and serves as a barrier to bacterial migration from the skin.

According to one embodiment of the invention, the cuff 602 is impregnated with an antimicrobial agent 604, such as silver, through IBAD or ion implantation. In a further embodiment, the dual ion beam assisted deposition system of FIG. 4 is employed to implant the catheter 600. The cuff portion 602 enhances the performance of the catheter 600 by further minimizing the possibility that the catheter will become microbially compromised or that a pathway will develop for microbial invasion of the patient.

As in the case of prior art catheters, the metal 604 provides an additional barrier to microbial migration. However, unlike prior art catheters, according to the present invention, the surface treatment is substantially nonleaching. Consequently, the antimicrobial properties of the catheter 600 do not significantly degrade over time. Thus, in contrast to prior art approaches which allow (or specifically require) the leaching or diffusion of an antimicrobial metal such as silver into a volumetric zone surrounding the device, the present invention serves to provide biomedical devices on which a antimicrobial metal is firmly anchored to a tissue-contacting surface.

Figure 6B:
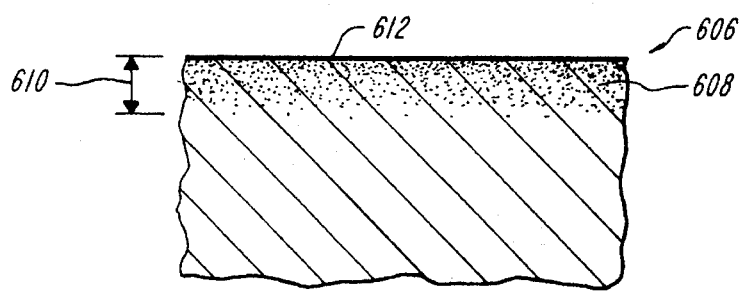
FIG. 6B shows a cross sectional view of a portion of a tissue interfacing surface of the cuff depicted in FIG. 6A wherein a tissue interfacing surface has been treated with an antimicrobial metal.

FIG. 6B shows a fragmentary section 606 on an enlarged scale, of the cuff portion 602. As indicated, the antimicrobial metal atoms 608 are implanted to a preferred depth 610. It is the concentration (defined in atoms/cm$^3$) of the implanted atoms 608 below the surface 612 that creates a subsurface fungicidal/bactericidal stratum. According to one embodiment of the invention, the antimicrobial metal atoms are implanted to have a density in the range of about $5\times10^{13}$ atoms/cm$^2$ to about $5\times10^{17}$ atoms/cm$^2$. However, the sufficiency of the concentration of the implanted atoms 608 to impart the desired antimicrobial properties to the cuff 602 depends, in part, on the material from which the cuff 602 is formed, e.g., metal, polymer, ceramic, etc. and in part on the specific antimicrobial metal atoms being implanted.

In the case where the cuff 602 is formed from a polyester such as Dacron® polyester, and where the antimicrobial metal is silver, a preferred concentration of the antimicrobial metal atoms 608 within the subsurface fungicidal/bactericidal stratum is at least about $1\times10^{15}$ atoms per square centimeter. The preferred penetration depth 610 of the subsurface fungicidal/bactericidal stratum within the individual polyester fibers is at least about 0.01 microns to about five microns. The penetration of antimicrobial atoms within the bulk porous material can extend as deep as 5000 microns or more, depending upon the porosity of the cuff material. The ion implantation process of the invention is effected over a time period from about one minute to about twenty hours, depending on a selected combination of total surface area to be treated, the desired ion dose and the ion beam current density being employed.

As discussed above, various apparatus such as depicted in FIGS. 2–5, can be employed to form the fungicidal/bactericidal stratum depicted in FIG. 6B. However, one significant difference between the IBAD approach of FIGS. 2–4 and the ion implantation approach of FIG. 5, is that less of a film is formed at the surface 612, when the ion implanter, of FIG. 5 is employed. Thus, where it is desired to have a substantial surface film, it is typically more advantageous to employ the IBAD approach of FIGS. 2–4. One such instance is where a multilayer antimicrobial film is to be formed.

As previously mentioned, it is generally difficult to form an adherent metal coating on a polymer. However, it is critical to the effective operation of the cuff 602 that a strong adherent bond is formed between the surfaces of the cuff 602 and the surface treatment 604. To enhance this bond, according to one embodiment of the invention, the surface treatment 604 is a multilayer treatment.

Figure 6C:
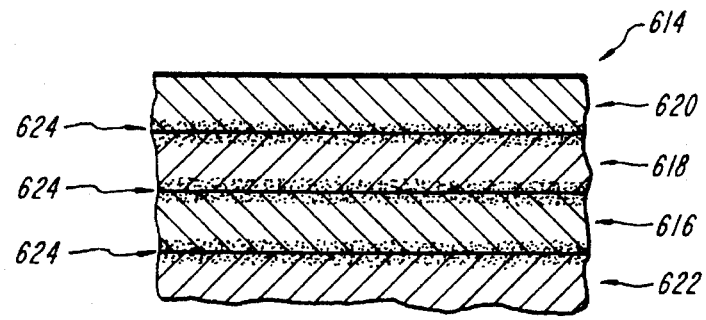
FIG. 6C shows a cross sectional view of a portion of a tissue interfacing surface of the cuff depicted in FIG. 6A wherein the tissue interfacing surface has been implanted with antimicrobial metal atoms, barrier atoms, and adhesion-promoting atoms.

FIG. 6C shows fragmentary section 614 of a cross sectional view on an enlarged scale of the surface 622 of catheter 602. Implanted into the surface 622 are a layer of titanium atoms 616, a layer of palladium atoms 618, and a layer of silver atoms 620. The titanium atoms 616 form an adhesion-promoting layer which enhances the bonding of the silver atoms 620 to the surface 622. The palladium atoms 618 provide a barrier for the titanium atoms 616, thus impeding galvanic interactions and/or diffusion between the silver atoms 620 and the titanium atoms 616. The silver atoms 620 provide the enhanced antimicrobial properties. In this way, the structure of FIG. 6C can provide the enhanced antimicrobial properties of silver, while exploiting the superior adhesion properties of titanium.

As can be seen at 624, each implanted layer is driven into the preceding layer. Not only does this facilitate proper adhesion, but it also ensures that the antimicrobial properties imparted by the silver atoms 620 persist in a subsurface stratum, thereby providing the long-lasting effects of the present invention.

Figure 7A:
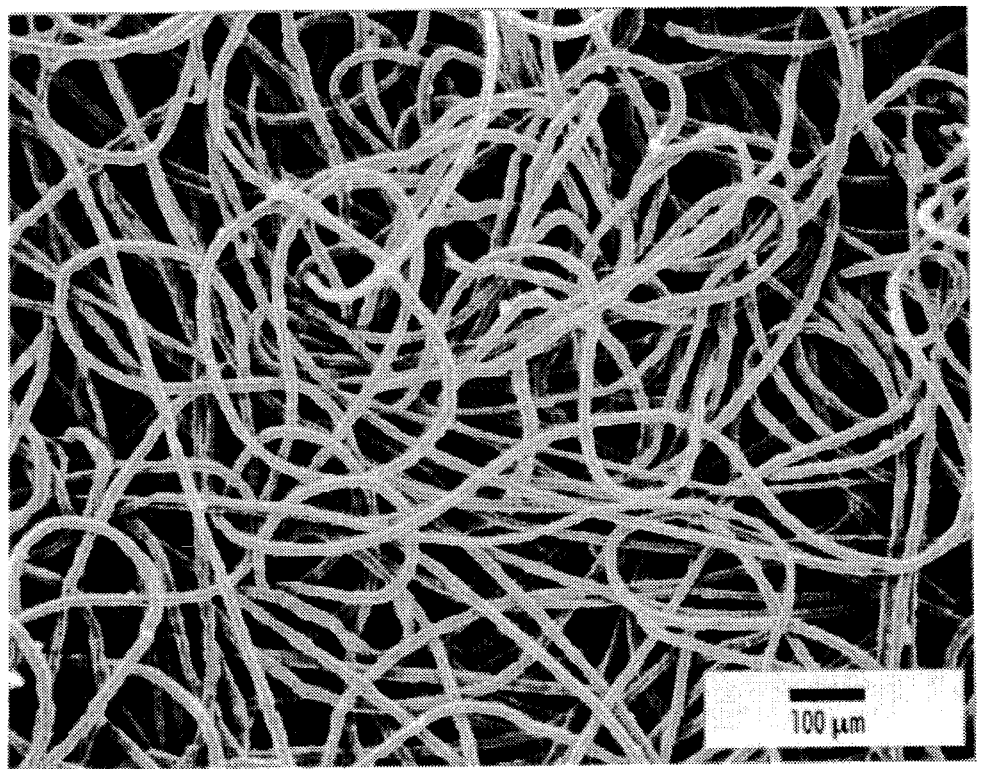
FIGS. 7a and 7b show an electron microscopic view of a portion of the subcutaneous cuff depicted in FIG. 6A.
Figure 7B:
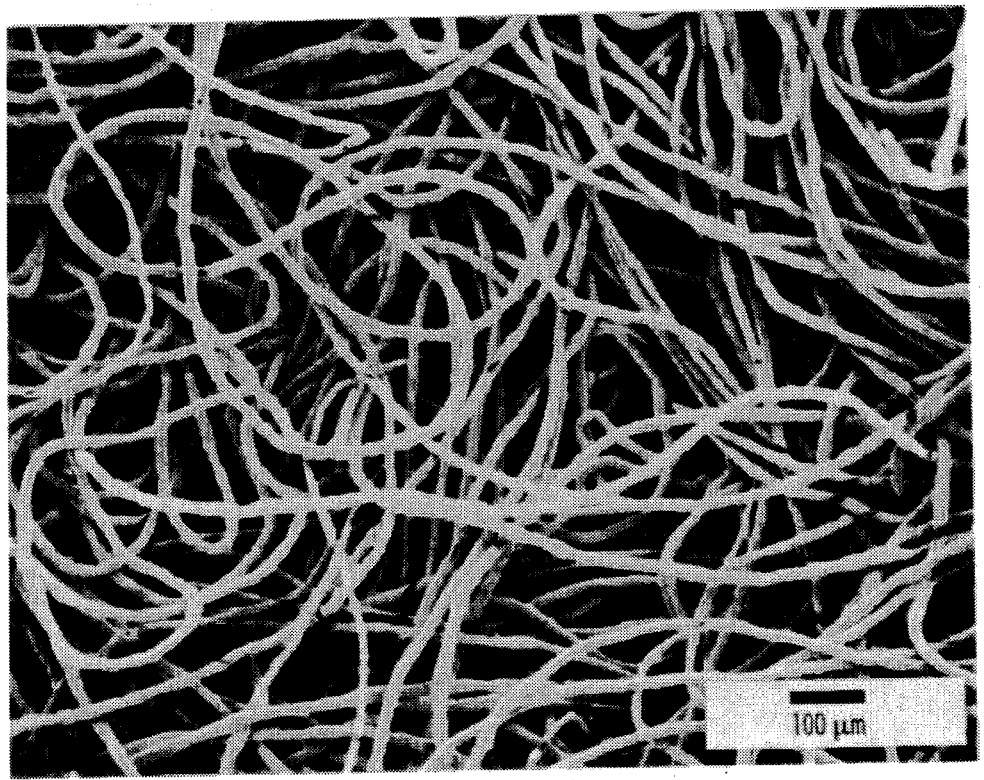

FIG. 7 shows an electron microscope view of an untreated catheter cuff 702 along with a treated cuff 704. An important function of the catheter cuff is to promote tissue ingrowth to form an anchor and a seal at the site where the cuff interfaces with tissue. The porous nature of the cuff material, which can be seen in FIG. 7, enhances this tissue ingrowth. Thus, it is important that antimicrobial agent does not disturb the porous nature of the cuff material. As can be seen at 704, an advantage of the present invention is that the antimicrobial metal surface treatment has virtually no effect on the fabric geometry of the catheter cuff material. The coating processes of the present invention do not fill the interstitial spaces between the fibers of the cuff material, but rather modify the surface of the fibers without substantially changing the porous nature of the cuff itself (which allows the cuff to continue to serve as a site for tissue ingrowth and anchorage). According to one preferred embodiment, the surface treatment of the invention penetrates the fabric geometry of the catheter cuff to a depth of approximately between 5 micrometers and 5000 micrometers.

Figure 8:
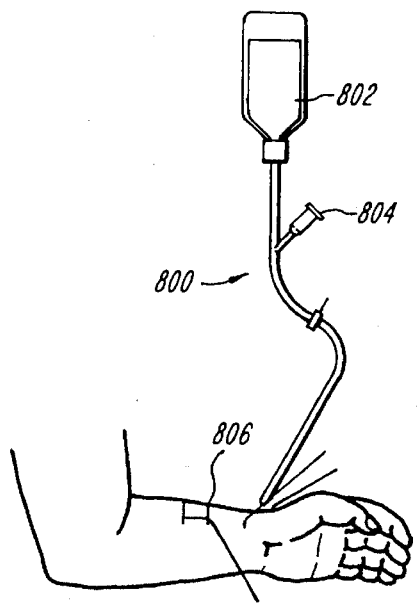
FIG. 8 is a schematic illustration of a typical intravenous infusion system in use.

FIG. 8 shows, a typical intravenous (I.V.) infusion system 800 for admitting a fluid 802 into an arm of a patient. If desired, other substances such as chemotherapy agents also can be added to the fluid 802 via a coupler 804 connected to the I.V. system 800. In this I.V. system 800, only the cannula 806 thereof is inserted into the vascular system of the patient. Hence, only this cannula portion 806 of the system 800 needs to be treated with a substantially nonleaching antimicrobial metal according to the invention.

Figure 9:
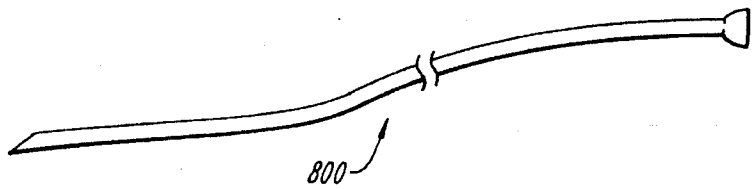
FIG. 9 illustrates a typical polymeric cannula for use in cardiovascular monitoring of a patient.

FIG. 9 shows an additional catheter 900, which is designed to be inserted substantially along its axial length. Such catheters can be used as cardiac catheters and pulmonary artery catheters. Where the catheter is designed to be substantially inserted into the body, it is advisable to treat the entire insertable portion with an antimicrobial metal.

Figure 10:
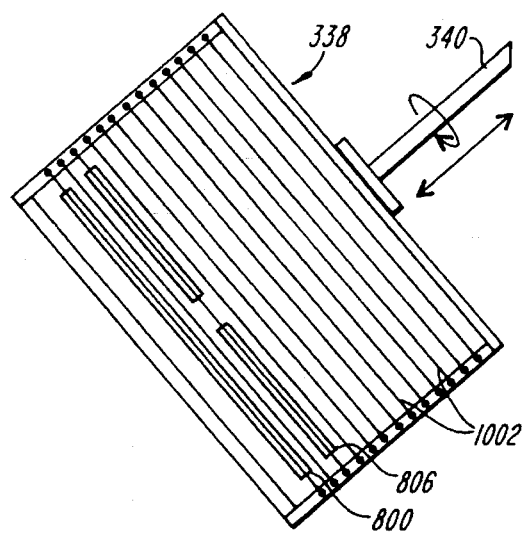
FIG. 10 is a schematic illustration of an alternative embodiment of the catheter holder depicted in FIG. 3.

As one skilled in the art will appreciate, the actual construction of the catheter holder 338 of FIG. 3 can vary depending on the device being implanted. By way of example, FIG. 10 depicts the catheter holder 338 formed as a cage. The cage 338 is lengthwise adjustable and is lengthwise provided with a plurality of mandrills 1002 to accommodate and securely hold a plurality of catheter tips 806 and catheters 900, respectively thereon. The catheter holder 338 preferably is rotated during the coating operation and is designed to be moved in translation between the antechamber 302 and the high-vacuum processing chamber 304 prior to the coating operation.

Figure 11:
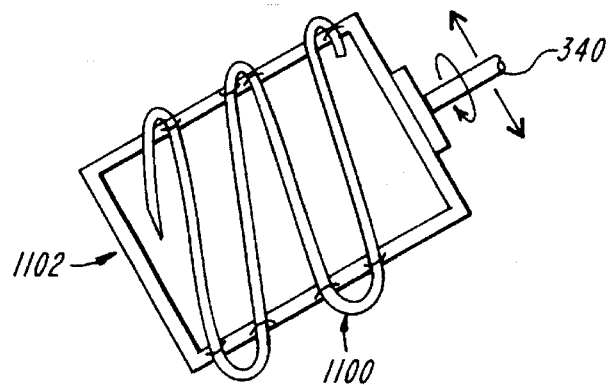
FIG. 11 is a view similar to FIG. 10 but illustrates the processing of a full length catheter according to the invention.

The dry-coating of the entire length of a rather long polymeric catheter 1100 is illustrated in FIG. 11. A square frame 1102 is shown being mounted to the end of the shaft 340. Depending on the relative sizes of the catheter 1100 versus the frame 1102, one or more catheters 1100 are loosely wound about the frame 1102. Longer catheters or a number of catheters can be processed on larger frames 1102.

Of course, as one skilled in the art will appreciate, any of the catheters 806, 900, and 1100 can include a subcutaneous cuff treated with an antimicrobial agent according to the process of the invention. The cuff can be formed and implanted prior to being fitted to the appropriate catheter. Alternatively, the cuff can be fitted to the catheter prior to implanting.

Additionally, while the invention has been described above in terms of certain polymeric implants, those skilled in the art will appreciate that according to other embodiments, the substantially nonleaching antimicrobial surface treatment of the invention can be applied to other biomedical devices such as introducers, diaphragms, valves, reservoirs, containers, IOL's and tubing. The treatment of the invention can also be applied to contact lenses, contact lens cases, toothbrushes and other personal hygiene products.

Following are five examples illustrating particular parameters employed for forming a substantially nonleaching antimicrobial surface treatment according to the invention.

EXAMPLE I

A polymeric catheter has been treated in the apparatus of FIG. 2 with the following operational parameters:

Evaporant: Copper, 1.0 angs./sec

Ion Beam: Argon, 30 μamps/cm$^2$, 2000 volts

Thickness of Coating: 0.5 micron

Processing Time: two hours

Vacuum Pressure in Processing Chamber: $10^{-6}$ torr

EXAMPLE II

A polymeric catheter has been treated over its entire length in the apparatus of FIG. 2 with the following operational parameters:

Evaporant: Silver, 6.0 angs./sec

Ion Beam: Argon, 100 μamps/cm$^2$, 500 volts

Thickness of Coating: 0.5 micron

Processing Time: one hour

Vacuum Pressure in Processing Chamber: $5\times10^{-7}$ torr

EXAMPLE III

A catheter formed of a polymer has been treated with the apparatus of FIG. 5, with the following parameters:

Catheter formed of silicone rubber material;

Subsurface fungicidal/bactericidal stratum:
  Penetration Depth: 0.1 micron
  Metal: Ag
  Dose: $5\times10^{16}$ ions/cm$^2$
  Vacuum in Implantation Chamber: $3.0\times10^{-6}$ torr
  Particle Energy: 50 keV
  Current Density 0.1 μA/cm$^2$ The process produced a low friction, non-tacky surface. The subsurface fungicidal/bactericidal stratum of the catheter remains biocompatible and substantially nonleaching, and was also thromboresistant.

EXAMPLE IV

A Teflon® felt catheter cuff was treated using a apparatus as shown in FIG. 5 with the following parameters:

Subsurface fungicidal/bactericidal stratum:
  Penetration Depth: 0.2 micron nominal for fibers
  Metal: Ag
  Dose: $5\times10^{16}$ ions/cm$^2$
  Vacuum in Implantation Chamber: $5.0\times10^{-6}$ torr
  Particle Energy:: 160 keV
  Current Density 2.0 μA/cm$^2$ The process produced a catheter cuff which remained porous with a subsurface antimicrobial stratum that was biocompatible and substantially nonleaching.

EXAMPLE V

A polyester velour catheter cuff was treated using a apparatus as shown in FIG. 2, with the following operational parameters:

|  | Layer 1 | Layer 2 | Layer 3 |
| --- | --- | --- | --- |
| Metal: | Ti | Pd | Ag |
| Deposition Rate: | 3.0 angs./sec | 3.0 angs./sec | 50.0 angs./sec |
| Ion Species: | Ar | Ar | Ar |
| Current Density: | 33 μamps/cm$^2$ | 50 μamps/cm$^2$ | 50 μamps/cm$^2$ |
| Ion Energy: | 500 eV | 1000 eV | 500 eV |
| Thickness: | 300 angstroms | 500 angstroms | 3500 angstroms |
| Temperature: | <150° C. | <150° C. | <150° C. |

Again, the surface modified catheter cuff remained porous with a antimicrobial coating that was biocompatible and nonleaching.

As described above, an antimicrobial metal surface treatment according to the invention is substantially nonleaching. Following is a summary of actual test data for a substantially nonleaching antimicrobial surface treatment according to the invention. The parameters tested include: adhesion to a component; leachability; tendency to form a zone of inhibition; and antimicrobial effectiveness. For the purposes of these tests, silver was employed as an antimicrobial metal. However, as discussed above, any of a plurality of such metals can be used.

Mechanical tests were performed to evaluate substrate surfaces treated with silver. The surfaces were evaluated using a series of qualitative tests: a stretch test, a bend test, a twist test, and a tape test. There was no removal of silver from the surface in tape tests nor after repeated bending and stretching of the substrate materials. The substrates were also exposed to a high temperature, high humidity environment for one week, and suffered no silver removal. Tests were conducted on treated surfaces of latex, polysulphone, polypropylene, polyethylene, polyimide, polyethylene terephthalate (PET), stainless steel, titanium and titanium alloys with no removal of silver.

The leachability of the treated surfaces was examined in Ringer's solution and other biological solutions. Four samples; treated and control polyester felt and treated and control polyester velour were evaluated. Measurements using Atomic Absorption Spectroscopy showed that minuscule amounts of silver and palladium were released from the samples, on the order of 0.12 ppm (or 120 μg/l) for both the felt and the velour. The release of Ti was less than the detection limits of the equipment. Also, approximately 0.08 μg/day/cm$^2$ of silver was released from the samples.

A zone of inhibition test was conducted to determine if the treated surface would affect bacteria at any distance from the surface and also, therefore, indicate a tendency for the silver to leach. Organisms tested include *P. aeruginosa* (PA), *S. epidermidis* (SE), and *E. coli* (EC). The silver treated and control silicone rubber samples did not set zones of inhibition against any organism. Table 1 depicts the zone of inhibition test results, and reflects the nonleaching nature of the surface treatment of the invention.

TABLE 1

In Vitro Zone of Inhibition Test Results

|  | E. coli | P. aeruginosa | S. epidermis |
|---|---|---|---|
| Ion implanted Ag | 0 mm | 0 mm | 0 mm |
| IBAD Ag | 0 mm | 0 mm | 0 mm |
| Control | 0 mm | 0 mm | 0 mm |
| Ag pellet | 4 mm | 6 mm | 4 mm |

Antimicrobial effectiveness testing was also conducted. This testing consisted of a battery of several tests in which treated surfaces on three different substrates were tested against six different organisms. First, silver treated silicone rubber flat samples were evaluated to test the effectiveness of the treated surfaces against *P. aeruginosa, S. epidermidis,* and *E. coli*. For these microbial challenge tests, growth of the test organisms on the test samples was scored based on the amount of growth present in comparison to the growth on the control plates. Both ion implanted and IBAD-produced silver surfaces caused lysis of all bacteria within three days of the challenge and caused 100% lysis in *P. aeruginosa* after only one day. Table 2 shows the results of the antimicrobial effectiveness testing.

TABLE 2

In Vitro Bacterial Challenge Test Results
(Percent of Bacterial Lysis)

|  | E. coli | P. aeruginosa | S. epidermis |
|---|---|---|---|
| Ion implanted Ag | 100% | 100% | 100% |
| IBAD Ag | 100% | 100% | 100% |
| Control | 0% | 0% | 0% |

Surface treated and control silicone rubber tubing samples were also tested for effectiveness against *Staphylococcus aureus* using a quantitative in vitro method. The testing of IBAD treated and control silicone rubber against *Staphylococcus aureus* demonstrated that the treated surface is very effective against this bacteria. After just 30 minutes of contact, the treated silicone rubber produced a 2.09±0.83 log kill of bacteria (n=6). Within 45 minutes of contact time, a 2.98±0.83 log kill of bacteria was achieved (n=9).

Figure 12:
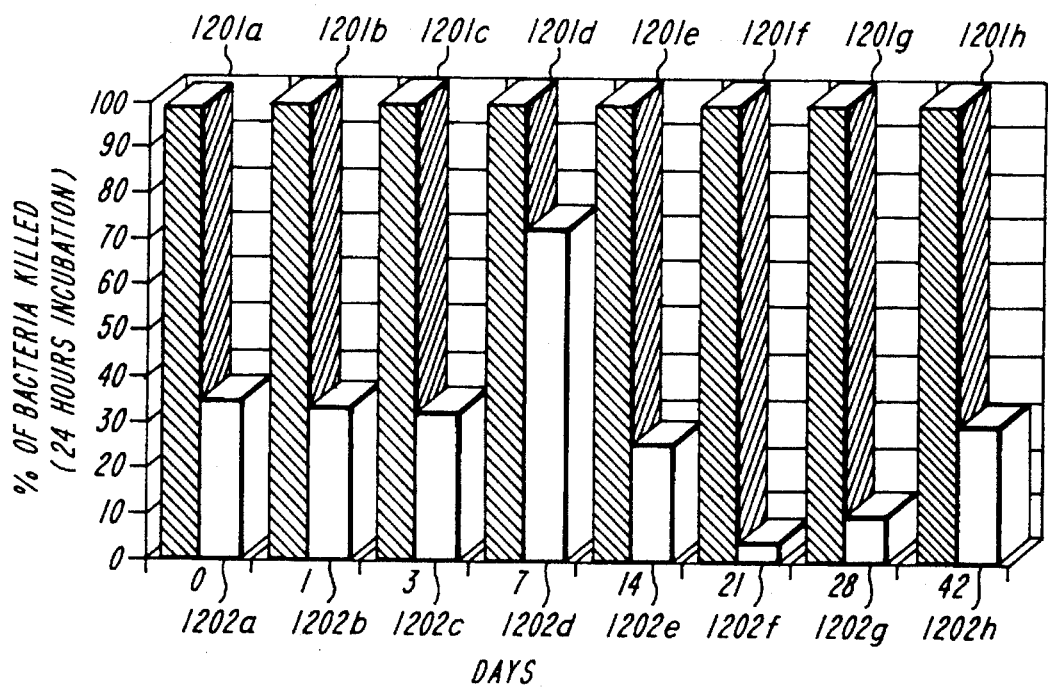
FIG. 12 is a graph illustrating long term antimicrobial properties of a catheter including a surface treatment according to the invention.

FIG. 12 illustrates the longer-term effectiveness of treated surfaces. The testing depicted in FIG. 12 was performed using silicone rubber catheters. The catheters were treated according to the invention and then soaked in saline solution for varying periods of time. Following soaking, their effectiveness against *Staphylococcus aureus* was tested. The treated catheters are represented at 1201*a*–1201*h*. The untreated control catheters are represented at 1202*a*–1202*h*. As can be seen, even where the treated catheter 1201*h* was soaked in saline solution for 42 days, it was nevertheless effective against *Staphylococcus aureus*.

An in vitro test was conducted on treated and control polyester velour to evaluate antimicrobial effectiveness. In this test, the ability of the test samples to cause lysis of *Staphylococcus epidermidis* and *Candida albicans* after one hour of contact was evaluated. Numbers of colony-forming units found after exposure of the *Staphylococcus epidermidis* and *Candida albicans* cultures to the treated polyester were found to drop significantly, a greater than 99.9% reduction.

Treated silicone rubber catheter samples were evaluated for encrustation and the potential to cause mucosal irritation following urinary tract implantation in test rabbits. Only one of the five recovered test samples showed any signs of mineral encrustation. The distal end of this one tip showed very minor encrustation. In contrast, control samples have become almost completely encrusted (i.e. nearly 100% of the surface covered) in the same period of time. Additionally, no signs of gross irritation were noted in the urethral tissues of any of the animals implanted with the treated catheters. Animals remained healthy throughout the test and gained weight normally, indicative of a safe, biocompatible device.

Cellular changes were graded in four areas on a scale of 0–4, with 0 indicating the least amount of damage. Scores from each area were totalled and averaged. Grading was as follows: 1–4 minimal; 5–8 mild; 9–11 moderate; 12–16 severe. This test produced an average score of 2 out of a possible 16, indicating a very minimal response. Finally, a clinical study was started to show the efficacy of a treated device in patients.

A preliminary clinical study of surface treated large-bore catheters was conducted by Dr. R. Bambauer at the University of Saarland in Hamburg, Germany. To date, seven patients have been exposed to silver-treated temporary hemodialysis catheters with a subclavian vein access for a period of up to 45 days. After removal the components were evaluated. The complication rates, including infection and thrombosis, are normally very high in this type of catheter used for hemodialysis. Test results indicate lack of any thrombus formation or bacterial attachment to the treated surfaces of catheters for the maximum amount of time implanted, 45 days. Scanning electron microscopy (SEM) studies of the catheter surfaces clearly show the silver-treated surfaces of the catheters to be free of any platelet deposits.

It is in this way the invention attains the objectives set forth above. In particular, a preferred embodiment of the invention provides a catheter including a subcutaneous cuff which is treated with a substantially nonleaching antimicrobial agent.

It is accordingly intended that all matter contained in the above description be interpreted as illustrative rather than in a limiting sense. It is also intended that the following claims cover all of the generic and specific features of the invention as described herein, and all statements of the scope of the invention which, as a matter of language, might be said to fall therebetween.

Having described the invention, what is claimed as new and secured by Letters Patent is:

1. A catheter formed from a polymeric material and having an outer surface, the surface having embedded by ion beam assisted deposition therein atoms of an antimicrobial metal, the atoms extending in a subsurface stratum to a predetermined depth from the outer surface to form a substantially nonleaching surface treatment.

2. The catheter of claim 1 wherein the antimicrobial metal comprises at least one of silver, chromium, aluminum, nickel, tungsten, molybdenum, platinum, iridium, gold, silver, mercury, copper zinc and cadmium.

3. The catheter of claim 1 wherein the atoms of the antimicrobial metal are embedded to a depth of less than about 5 microns to ensure that the atoms of the antimicrobial metal are substantially nonleaching.

4. The catheter of claim 1 further comprising a uniform coating of the antimicrobial metal formed on the outer surface of the material.

5. The catheter of claim 1 wherein the outer surface has disposed between it and the atoms of the antimicrobial metal, atoms of an adhesion-promoting material which enhance the binding of the antimicrobial metal to the outer surface.

6. The catheter of claim 5 wherein the adhesion-promoting material comprises titanium.

7. The catheter of claim 5 wherein the adhesion-promoting material has disposed between it and the atoms of the antimicrobial metal, atoms of a barrier-forming material which form at least one of a barrier to degradation or diffusion of the adhesion-promoting atoms and an impediment to galvanic interaction between the antimicrobial metal and the adhesion-promoting material.

8. The catheter of claim 7 wherein the barrier-forming material comprises palladium.

9. The catheter of claim 1 wherein the outer surface has disposed between it and the atoms of the antimicrobial metal, atoms of titanium and palladium wherein the titanium atoms are predominantly located adjacent to the surface and interposed between the surface and the antimicrobial metal, and palladium atoms are predominantly interposed between the titanium atoms and the antimicrobial metal.

10. The catheter of claim 1 wherein the outer surface is a subcutaneous catheter cuff surface.

11. The catheter of claim 10 wherein the subcutaneous catheter cuff is formed from a porous polymeric material.

12. The catheter of claim 10 wherein the cuff is formed from a polymeric material.

13. The catheter of claim 11 wherein the surface has tissue interfacing fibers that form a fabric geometry having interstitial spaces between the fibers, and wherein the embedded atoms of the antimicrobial metal are embedded in the fibers, without filling the interstitial spaces in the fabric geometry, thus preserving the porosity of the subcutaneous cuff.

14. The catheter of claim 10 wherein the material comprises at least one of polyesters, fluropolymers, polyurethanes and silicones.

15. A subcutaneous cuff formed from a porous polymeric material and having fibers that form a fabric geometry having interstitial spaces between the fibers, each of the fibers having an outer surface the outer surfaces having embedded by ion beam assisted deposition therein atoms of an antimicrobial metal, the atoms extending in a subsurface stratum to a predetermined depth from the outer surface of each fiber to form a substantially nonleaching surface treatment, and the interstitial spaces between the fibers being unchanged by the embedded atoms of the antimicrobial metal.

16. The subcutaneous cuff of claim 15 wherein the antimicrobial metal comprises at least one of silver, chromium, aluminum, nickel, tungsten, molybdenum, platinum, iridium, gold, silver, mercury, copper, zinc and cadmium.

17. The subcutaneous cuff of claim 15 wherein the atoms of the antimicrobial metal are embedded into the outer surfaces of the tissue interfacing fibers to a depth of between about 0.01 microns and 5 microns to ensure that the antimicrobial metal is substantially nonleaching.

18. The subcutaneous cuff of claim 15 further comprising coating of the antimicrobial metal formed on the outer surfaces of the tissue interfacing fibers.

19. The subcutaneous cuff of claim 15 wherein the outer surfaces have disposed between them and the atoms of the antimicrobial metal, atoms of an adhesion-promoting material which enhance the binding of the antimicrobial metal to the outer surfaces.

20. The subcutaneous cuff of claim 19 wherein the adhesion-promoting atoms comprise titanium.

21. The subcutaneous cuff of claim 19 wherein the adhesion-promoting material has disposed between it and the atoms of the antimicrobial metal, atoms of a barrier-forming material which form at least one of a barrier to degradation or diffusion of the adhesion-promoting atoms and an impediment to galvanic interaction between the antimicrobial metal and the adhesion-promoting atoms.

22. The subcutaneous cuff of claim 21 wherein the barrier-forming atoms comprise palladium.

23. The subcutaneous cuff of claim 15 wherein the outer surfaces have disposed between them and the atoms of the antimicrobial metal, atoms of titanium and palladium wherein the titanium atoms are predominantly located adjacent to the surface and interposed between the surface and the antimicrobial metal, and the palladium atoms are predominantly interposed between the titanium atoms and the antimicrobial metal.

24. The subcutaneous cuff of claim 14 wherein the polymeric material comprises at least one of polyesters, fluropolymers, polyurethanes, and silicones.

25. The subcutaneous cuff of claim 14 wherein the atoms of the antimicrobial metal are embedded in the surfaces of fibers, which extend into the fabric geometry to a depth of greater than about 5 microns.

26. The subcutaneous cuff of claim 14 wherein the outer surfaces have disposed between them and the atoms of the antimicrobial metal, atoms of an adhesion-promoting material which enhance the binding of the antimicrobial metal to the outer surfaces, without filling in the interstitial spaces.

27. The subcutaneous cuff of claim 26 wherein the coating of the adhesion-promoting material has disposed between it and the atoms of the antimicrobial metal, atoms of a barrier-forming material which form at least one of a barrier to degradation or diffusion of the adhesion promoting atoms and an impediment to galvanic interaction between the antimicrobial metal and the adhesion-promoting atoms without filling the interstitial spaces.

28. A subcutaneous cuff formed from a porous polymeric material and having tissue interfacing fibers that form a fabric geometry having interstitial spaces between the fibers, each of the fibers having an outer surface, the outer surfaces having embedded therein atoms of an adhesion-promoting material and formed thereon a coating of the adhesion-promoting material, the coating of the adhesion-promoting material having embedded therein atoms of a barrier-promoting material and formed thereon a coating of the barrier-promoting material, the barrier-promoting material having atoms of silver metal embedded therein, wherein the adhesion-promoting material enhances the bonding of the silver to the outer surfaces, and the barrier material reduces galvanic interaction between the silver and the adhesion-promoting material.

29. A subcutaneous cuff for interfacing with subcutaneous tissue formed from a porous polymeric material and having an outer surface, having embedded by ion beam assisted deposition therein atoms of an antimicrobial metal, the atoms extending in a subsurface stratum to a predetermined depth from the outer surface to form a substantially non-leaching surface treatment.

30. The cuff of claim 29 wherein the outer surface has disposed between it and the atoms of the antimicrobial metal, atoms of an adhesion-promoting material, wherein the atoms of the adhesion-promoting material enhance the binding of the antimicrobial metal to the outer surface.

31. The cuff of claim 30 wherein the atoms of the adhesion-promoting material has disposed between it and the atoms of the antimicrobial metal, atoms of a barrier-forming material, wherein the atoms of the barrier-forming material form at least one of a barrier to degradation or diffusion of the adhesion-promoting atoms and an impediment to galvanic interaction between the antimicrobial metal atoms and the adhesion-promoting atoms.

32. The cuff of claim 31 wherein the barrier-forming material comprises palladium.

33. The cuff of claim 29 wherein the antimicrobial metal comprises at least one of silver, chromium, zirconium, aluminum, nickel, tungsten, molybdenum, tantalum, platinum, iridium, gold, silver, mercury, copper, zinc and cadmium.

34. The cuff of claim 30 wherein the adhesion-promoting material comprises titanium.

35. The cuff of claim 29 wherein the polymeric material comprises at least one of polyesters, fluropolymers, silicones, and polyurethanes.

* * * * *